US008569644B2

(12) United States Patent
Nierle et al.

(10) Patent No.: US 8,569,644 B2
(45) Date of Patent: Oct. 29, 2013

(54) PROCESS AND APPARATUS FOR ANALYSING AND SEPARATING GRAIN

(75) Inventors: Michael Nierle, Bad Gottleuba (DE); Peter Nallen, Banagher (IE)

(73) Assignee: Minch Malt Limited (IE)

( * ) Notice: Subject to any disclaimer, the term of this patent is extended or adjusted under 35 U.S.C. 154(b) by 228 days.

(21) Appl. No.: 12/513,207

(22) PCT Filed: Nov. 13, 2008

(86) PCT No.: PCT/EP2008/065504
§ 371 (c)(1),
(2), (4) Date: Jan. 4, 2011

(87) PCT Pub. No.: WO2009/063023
PCT Pub. Date: May 22, 2009

(65) Prior Publication Data
US 2011/0089090 A1    Apr. 21, 2011

(30) Foreign Application Priority Data
Nov. 13, 2007    (IE) .................................. S2007/0825

(51) Int. Cl.
*B07C 5/00*        (2006.01)
(52) U.S. Cl.
USPC ........... 209/576; 209/577; 209/579; 209/581; 250/339.01; 250/339.07; 250/341.7
(58) Field of Classification Search
USPC ............. 209/571, 577, 579, 587; 250/339.01, 250/339.07
See application file for complete search history.

(56) References Cited

U.S. PATENT DOCUMENTS

| | | | |
|---|---|---|---|
| 2,933,613 A * | 4/1960 | Powers ..................... | 250/214 R |
| 4,547,725 A | 10/1985 | Oetiker et al. | |
| 4,806,764 A | 2/1989 | Satake | |
| 5,245,188 A * | 9/1993 | Satake et al. ............... | 250/341.7 |
| 5,406,084 A | 4/1995 | Tobler et al. | |
| 5,733,592 A | 3/1998 | Wettstein et al. | |
| 5,779,058 A * | 7/1998 | Satake et al. .................. | 209/581 |
| 5,865,990 A | 2/1999 | Novak et al. | |
| 6,483,583 B1 | 11/2002 | Wright et al. | |
| 6,646,264 B1 | 11/2003 | Modiano et al. | |
| 6,847,447 B2 * | 1/2005 | Ozanich ........................ | 356/326 |
| 2009/0032444 A1* | 2/2009 | Koyama et al. ............... | 209/586 |
| 2010/0089804 A1* | 4/2010 | Lambert et al. ............... | 209/576 |
| 2010/0096299 A1* | 4/2010 | Adams et al. .................. | 209/577 |

FOREIGN PATENT DOCUMENTS

FR    2632879    12/1989

OTHER PUBLICATIONS

International Search Report for PCT/EP2008/065504, mailed Feb. 13, 2009.

* cited by examiner

*Primary Examiner* — Terrell Matthews
(74) *Attorney, Agent, or Firm* — Choate, Hall & Stewart LLP; Andrea L. C. Robidoux; Paul A. Nuzzi

(57) ABSTRACT

A process and apparatus for analyzing quantities of grain in-line and separating the grain into batches on the basis of one or more grain parameter values is disclosed. The grain is separated in-line on the basis of the grain parameter value thus allowing the grain to be separated into homogeneous batches.

10 Claims, 12 Drawing Sheets

PROCESS AND APPARATUS FOR ANALYSING AND SEPARATING GRAIN

This application claims the benefit under 35 U.S.C. §371 of International Application No. PCT/EP2008/065504, filed Nov. 13, 2008, which claims priority to Ireland Patent Application No. S2007/0825, filed Nov. 13, 2007, the entire contents of each of which are hereby incorporated herein by reference.

INTRODUCTION

The present invention relates to a process and apparatus for analysing quantities of grain in-line and separating the grain into batches on the basis of one or more grain parameter values In the specification the term "in-line" refers to a procedure which can be carried out while an apparatus is running and does not require the apparatus to be shut down during the procedure.

The quality of the grain used is an important aspect of all types of grain processing. For example, in malting, barley quality has a significant effect on the resultant malt quality. Two of the most critical factors which determine barley quality are grain moisture and protein content and these factors therefore require special attention prior to storage and processing.

The moisture content of the grain has an important role in its health and viability during storage. Harvested barley, for example, with a moisture content of greater that 14% by weight of the barley, needs to be dried to reduce the moisture level to between 12% and 13% prior to storage. The exact level depends on expected duration of storage until processing and storage temperature. The drying process must be rather gentle and thus air temperatures not exceeding 65° C. to 70° C. are utilised depending on the initial grain moisture content. The final grain temperature should not exceed 40° C., otherwise irreversible damage of the embryo and other living tissue in the barley will hamper the downstream malting process.

The protein levels in barley determine the resultant protein levels in the malt and thus the malt quality. It has been found that barley which has a protein content in the range of between 9.5% to 12% dry matter would yield malt having a protein level in the region of between 9.2% and 11.7% dry matter. The protein content has an impact on the water uptake during steeping and the degree and quality of endosperm modification during germination thus a batch of grain having uneven protein contents would result in uneven germination of the batch. This will affect the colour, aroma and flavour of the malt, as well as downstream processing of the malt.

Many methods are presently available for measuring the protein and moisture content of grain. Moisture content can be measured by weighing batches of grain before and after drying, however the main drawback of this process is that it is very time-consuming, with each batch analysis taking between 2 and 3 hours. Rapid methods based on this principle such as the Sartorious method have been developed and this method for example only requires 20 to 30 minutes of analysis time including preparation but has been found to be less accurate. Another rapid method for measuring moisture content is the "HOH-Express" (Heckmann company, Germany). This method only takes three to five minutes and has good accuracy but requires time consuming automatic or manual sampling beforehand. Previous methods of measuring protein content include the Kjeldahl method, which involves nitrogen analysis. This method is also very time consuming and requires sampling.

In the case of all of the above methods, a few samples from a batch are taken, these quantities are analysed in accordance with these methods and an average result is calculated for the particular grain parameter value being measured, i.e. protein content, moisture content. The average value for the grain parameter value measured however is dependent on the type of grain in each sample and generally may not be representative of the overall batch of grain.

An improved apparatus for measuring grain parameters is that disclosed in U.S. Pat. No. 5,406,084. This document discloses an NIR measuring process and apparatus for measuring constituents of pourable foodstuffs in-line. After the measurements are obtained, however they are averaged to provide an average value for a particular constituent for a batch of grain. It is envisaged therefore that this process and apparatus would lead to inhomogeneity within grain batches.

Accordingly, there is a need for a more effective process and apparatus for analysing and for separating grain to provide more homogeneous batches of grain on the basis of a particular grain parameter.

STATEMENTS OF INVENTION

According to the invention, there is provided a process for analysing quantities of grain in-line and separating the grain into batches on the basis of one or more grain parameter values, the process comprising:
  delivering an optically dense grain layer continuously past an in-line measurement area;
  analysing a quantity of the grain by emitting light onto the grain layer, the light being reflected from the quantity of grain passing the in-line measurement area and detecting the light reflected from the quantity of grain to provide a spectrum of the quantity of grain;
  converting the spectrum into the or each grain parameter value; and
  separating the grain into batches by sorting the grain quantity on the basis of the or each grain parameter value;
  characterised in that:
  the grain is separated in-line on the basis of the or each grain parameter value.

The advantage of this process is that more accurate separation of the grain on the basis of a specified grain parameter value can be achieved. Thus, after separation, grain quantities with similar values for a specific grain parameter can be stored together as homogeneous batches. This obviates any of the drawbacks associated with inhomogeneity of grain. For example, in the case of harvested barley, batches of barley with similar moisture contents can be stored accordingly in order to optimise the drying performance as well as ensuring the required viability of the grain after the drying process. Additionally, barley with homogenous protein contents, can be stored and processed resulting in more even modification.

A further advantage of the invention is that the values measured for each of the quantities or sub-lots of grain can be traced. Thus documentation for each specific process can be made available to clients, which is important in terms of the Hazard Analysis Critical Control Point (HACCP) (an internationally recognized system for ensuring that food products are safe and wholesome to eat) and food safety policies.

In one embodiment of the invention, separating the grain in-line comprises the steps of:
  storing one or more grain threshold values;

comparing the or each grain parameter value to the corresponding stored grain threshold value;
generating a signal based on the comparison between the or each grain parameter value and the corresponding grain threshold value;
using the signal to effect automatic delivery of the grain quantity to a predetermined location on the basis of the grain parameter value.

In another embodiment of the invention, the optically dense grain layer is delivered at a speed of between 0.5 and 2.5 m/s. In a further embodiment of the invention, the optically dense grain layer is delivered at a speed of between 1 and 2 m/s. The advantage of these speeds is that they allow rapid analysis and separation of the grain. The process is therefore less time consuming and more cost effective.

Preferably, the light is emitted continuously onto the optically dense grain layer.

In one embodiment of the invention, the light is emitted at a wavelength of between 200 and 2000 nm In another embodiment of the invention, the light is emitted at a Near Infrared (NIR) spectral region of between 780 nm and 2000 nm and an NIR spectrum is provided.

In a further embodiment of the invention, the light is emitted at a wavelength of between 900 and 1500 nm In one embodiment of the invention, the light is detected from the quantity of grain in a time of between 15 and 70 milliseconds.

In another embodiment of the invention, the light detected from the quantity of grain in a time of between 30 and 50 milliseconds. Thus as the light is rapidly detected, this also accelerates the process for analysing and separating the grain.

According to the invention, there is also provided an apparatus for analysing quantities of grain in-line and separating the grain into batches on the basis of one or more grain parameter values, the apparatus comprising:
  means for continuously delivering an optically dense grain layer past an in-line measurement area;
  a light source for emitting light onto the grain layer, the light being reflected from the quantity of grain passing the in-line measurement area;
  a sensor unit for detecting the light reflected from the quantity of grain to provide a spectrum of the quantity of grain;
  means for converting the spectrum into the or each grain parameter value; and
  means for separating the grain into batches by sorting the grain quantity on the basis of the or each grain parameter value;
characterised in that:
  the apparatus further comprises in-line means for separating the grain on the basis of the or each grain parameter value.

In one embodiment of the invention, the in-line grain separating means comprises:
  a controller comprising one or more stored grain threshold values;
  a transmitter for transmitting the or each grain parameter value to the controller; wherein
  the controller compares the or each grain parameter value to the corresponding stored grain threshold value;
  the controller generates a signal based on the comparison between the or each grain parameter value and the corresponding grain threshold value; and
  the controller transmits the signal to at least one exit means such that the signal is used to affect automatic delivery of the quantity of the grain via the exit means to a predetermined location on the basis of the grain parameter value.

In another embodiment of the invention, the exit means comprises:
  a controlled slide having an open position and a closed position and connected to a first silo; and
  an end slide connected to a second silo; wherein
  the controller communicates with the controlled slide and controls the position of the controlled slide to allow or prevent the quantity of grain exiting via that slide; such that
  when the controlled slide is in the closed position the quantity of grain will exit the apparatus via the end slide.

In a further embodiment of the invention, the controlled slide is pivotally movable between the open position and the closed position.

In one embodiment of the invention, the controlled slide remains in the same position during detection of grain parameter values which are consistently lower or higher than the grain threshold value.

In another embodiment of the invention, the controller transmits a signal to the controlled slide to prepare to change position and triggers a pre-determined lag time $t_{lag}$ to begin upon detection of a sufficient change in the grain parameter value such that the grain parameter value crosses over the grain threshold value.

In a further embodiment of the invention, the controller transmits the signal to the controlled slide to change position after detection of a series of sufficiently changed grain parameter values during the lag time $t_{lag}$.

In this embodiment of the invention, the position of the controlled slide changes at a time equal to $t_{lag}+t_n$; wherein $t_n$ is equal to the period of time allowed for the final grain quantity analysed during the lag time $t_{lag}$ to travel from the sensor unit to the controlled slide. The advantage of these particular embodiments is that they allow rapid separation of the grain in-line while overcoming possible limitations which could be envisaged due to the mechanical nature of the apparatus. Thus as the slide only changes position after detection of a series of sufficiently changes grain parameter values this prevents constant oscillation of the slide or other suitable opening means.

In one embodiment of the invention, the controller is a programmable logic controller In another embodiment of the invention, the delivery means delivers the optically dense grain layer at a speed of between 0.5 and 2.5 m/s.

In a further embodiment of the invention, the delivery means delivers the optically dense grain layer at a speed of between 1 and 2 m/s.

In one embodiment of the invention, the delivery means comprises a dosing slide which is slideably adjustable within the delivery means to provide the optically dense grain layer. The advantage of the dosing slide is that it controls the flow and consistent speed of the grain thus allowing the sensor unit to detect light from an appropriately dense grain layer as it passes by the in-line measurement area.

In another embodiment of the invention, the delivery means comprises one or more of a grain in-feed chute and a conveyor.

In this embodiment of the invention, the grain in-feed chute is positioned at an angle of between 45° and 90° relative to the conveyor.

In another embodiment of the invention, the grain in-feed chute further comprises a grain quantity divider having a plurality of chutes providing channels for flow of individual grain quantities.

In one embodiment of the invention, the light source emits light continuously onto the optically dense grain layer.

In another embodiment of the invention, the light source emits light at a wavelength range of between 200 and 2000 nm.

In a further embodiment of the invention, the light source emits light at a Near Infrared (NIR) spectral region of between 780 nm and 2000 nm and an NIR spectrum is provided.

In a still further embodiment of the invention, the light source emits light at a wavelength range of between 900 and 1500 nm.

In one embodiment of the invention, the sensor unit is mounted at an angle in the region of 90° to the delivery means.

In one embodiment of the invention, the grain parameters are selected from the group comprising one or more of grain protein content, grain moisture content, starch extract content, β-glucan content, beta-amylase content and mycotoxine content.

DETAILED DESCRIPTION OF INVENTION

The invention will be more clearly understood from the following description of some embodiments thereof, given by way of example only, with reference to the accompanying drawings, in which:—

Figure 1:
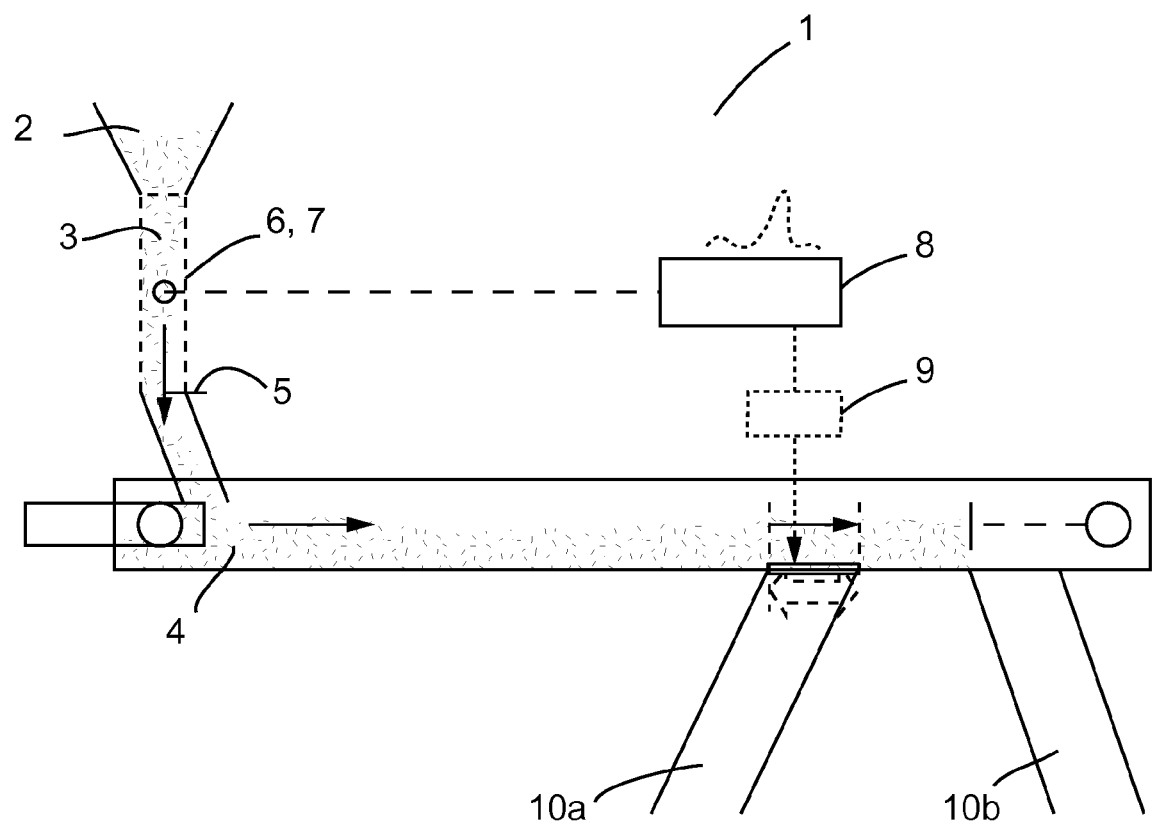
FIG. 1 is a schematic of the apparatus of the invention.

Referring to FIG. 1 there is illustrated a schematic of the apparatus of the invention, indicated generally by reference numeral 1. The apparatus comprises a grain in-feed hopper 2 and a grain in-feed chute 3 for continuous delivery of grain into the apparatus 1. The apparatus 1 also comprises a conveyor 4 for continuous delivery of grain through the apparatus 1. A dosing slide 5 which provides consistent and even grain flow through the apparatus 1 is provided either within the grain in-feed chute 3 as shown or at any suitable position within the conveyor 4. The dosing slide 5 can be adjusted manually to control the flow of grain through the apparatus 1 and thus provide a consistent grain flow at a fixed speed and an optically dense grain layer for analysis. In the specification the term "optically dense grain layer" refers to a dense grain layer of at least 10 mm without any gaps between the grain.

The apparatus 1 further comprises a light source 6 for emitting light onto the grain layer and a sensor unit 7 for detecting light reflected from a quantity of the grain layer and providing a spectrum from the quantity of grain. The light source 6 can optionally be positioned within the sensor unit 7. The sensor unit 7 can also comprise a measuring head (not shown) and a black/white referencing system (not shown). A spectrometer 8 is further provided for converting the spectrum into an electrical signal which is subsequently converted into the respective grain parameter value for that quantity using specifically designed software. The grain parameter values generated by the spectrometer 8 are transmitted to a controller 9 generally by means of a transmitter (not shown).

The apparatus 1 further comprises one or more slides 10a, 10b through which the quantities of grain can exit the apparatus 1. The controlled slide 10a is controlled by the controller 9 and is either opened or shut depending on the grain parameter value for that particular quantity. When the controlled slide 10a is open, the quantity of grain passing over the controlled slide 10a at that time will exit via the controlled slide 10a to a storage silo (not shown).

Figure 12:
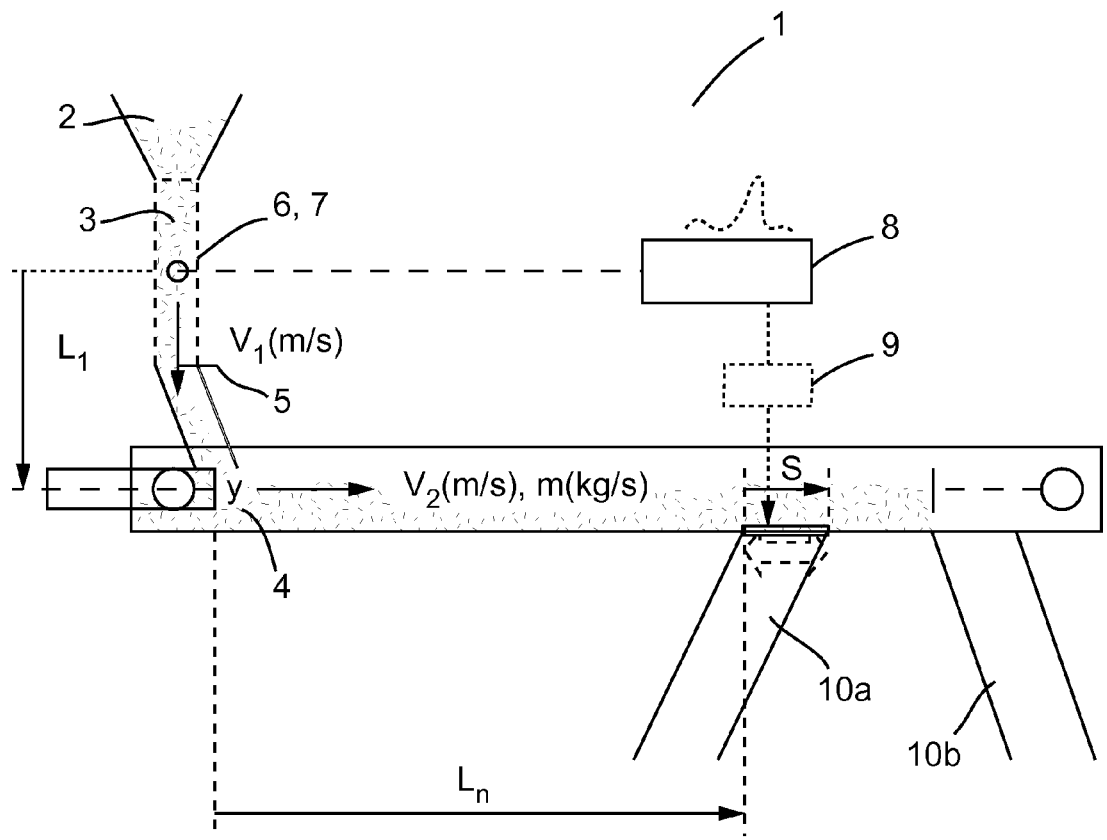
FIG. 12 is a further schematic of the apparatus with each of the parameters required to programme the controller of the apparatus.

The controller 9 will also control when the controlled slide 10a is to open and for how long the controlled slide 10a is to stay open and further details of this are discussed in relation to FIG. 12. Any quantities of grain which are not within the specified parameter range are delivered via the conveyor 4 to the end slide 10b, where they will exit the apparatus via the end slide 10b to another storage silo (not shown), thus separating the grain in-line on the basis of a specific parameter.

Figure 2:
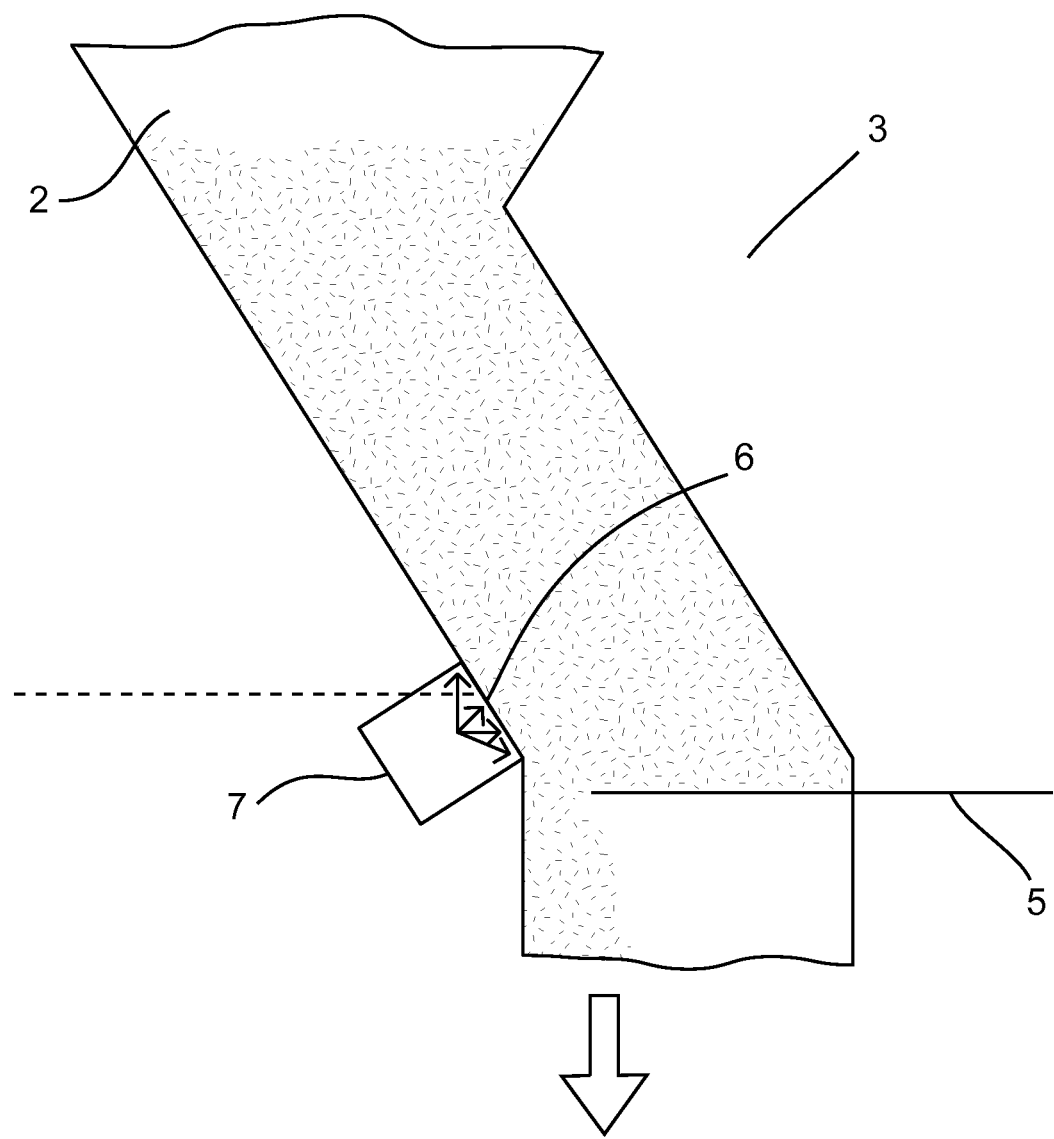
FIG. 2 is a view of the grain in-feed hopper and grain in-feed chute of one embodiment of the invention.

FIG. 2 shows a more detailed view of the grain being fed into the grain in-feed chute 3 by the grain in-feed hopper 2. The light source 6 is housed within the sensor unit 7. The sensor unit 7 is positioned exterior of the grain in-feed chute so as to emit light onto an area of the grain in-feed chute referred to as the measurement area. The sensor unit 7 should also be positioned at an angle to the flow of the grain in such a manner that the emitted light will be accurately reflected from the grain layer passing by. A grain in-feed chute angle of between 45° and 90° has been found to be most suitable. The dosing slide 5 is positioned downstream of the sensor unit 7 and is slideably adjustable within the grain in-feed chute to ensure that an optically dense grain layer is provided for measurement by the sensor unit 7.

Figure 3:
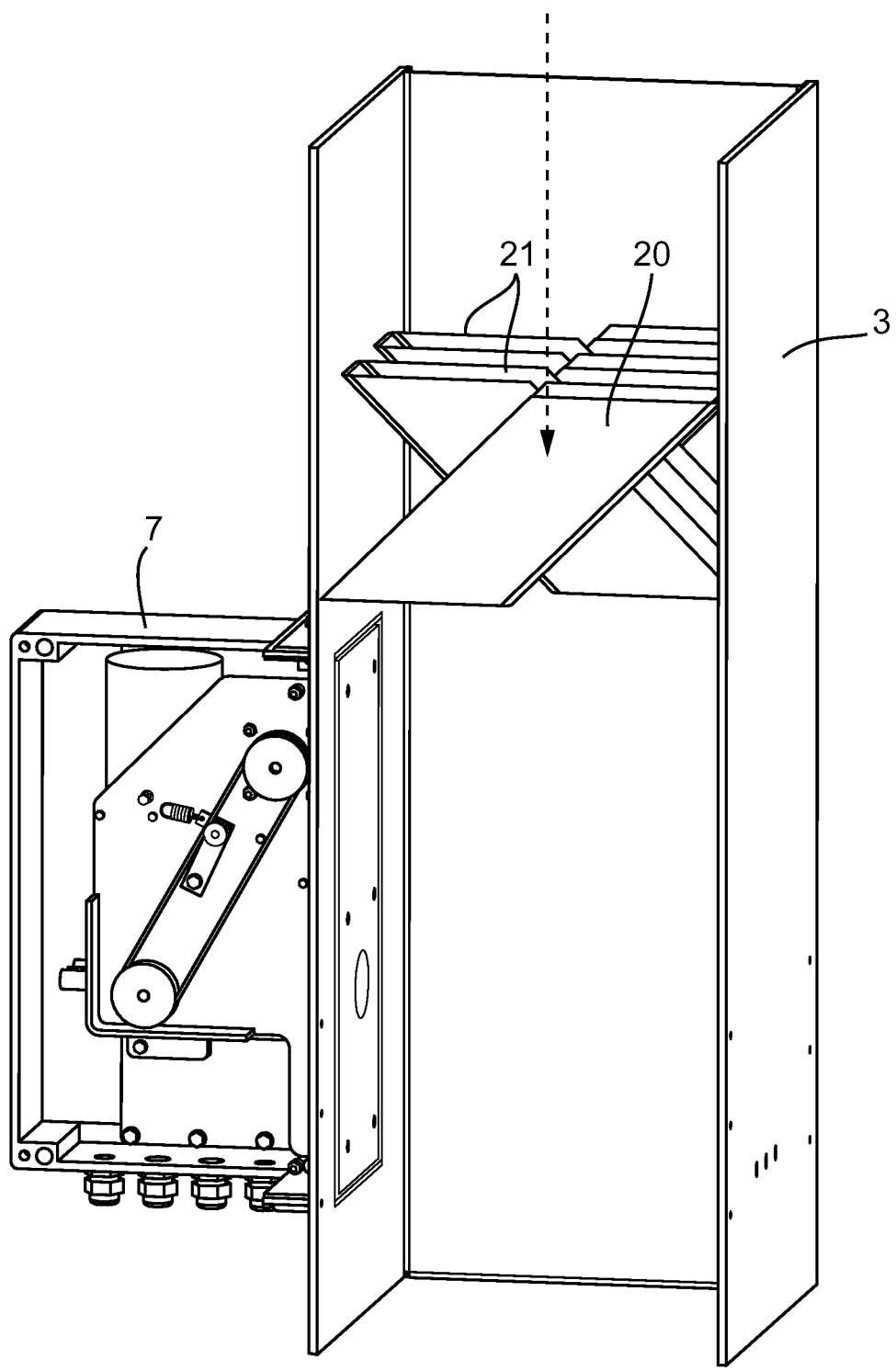
FIG. 3 is a view of the grain in-feed chute of another embodiment of the invention.

FIG. 3 shows an alternative embodiment of the grain in-feed chute 3. In this embodiment a grain quantity divider 20 is provided within the grain in-feed chute 3. The grain quantity divider 20 comprises a plurality of chutes 21, through which a quantity of grain can flow prior to being mixed homogeneously before passing the sensor unit 7. The grain quantity divider 20 ensures that the grain quality within the grain mass differential passing by the sensor unit 7 will be homogenous across the diameter of the respective chute 21. The quantity divider 20 is particularly suitable for higher grain flows and in particular grain flows of greater than approximately 400 t/h. A dosing slide 5 can also be provided to control grain flow.

Figure 4:
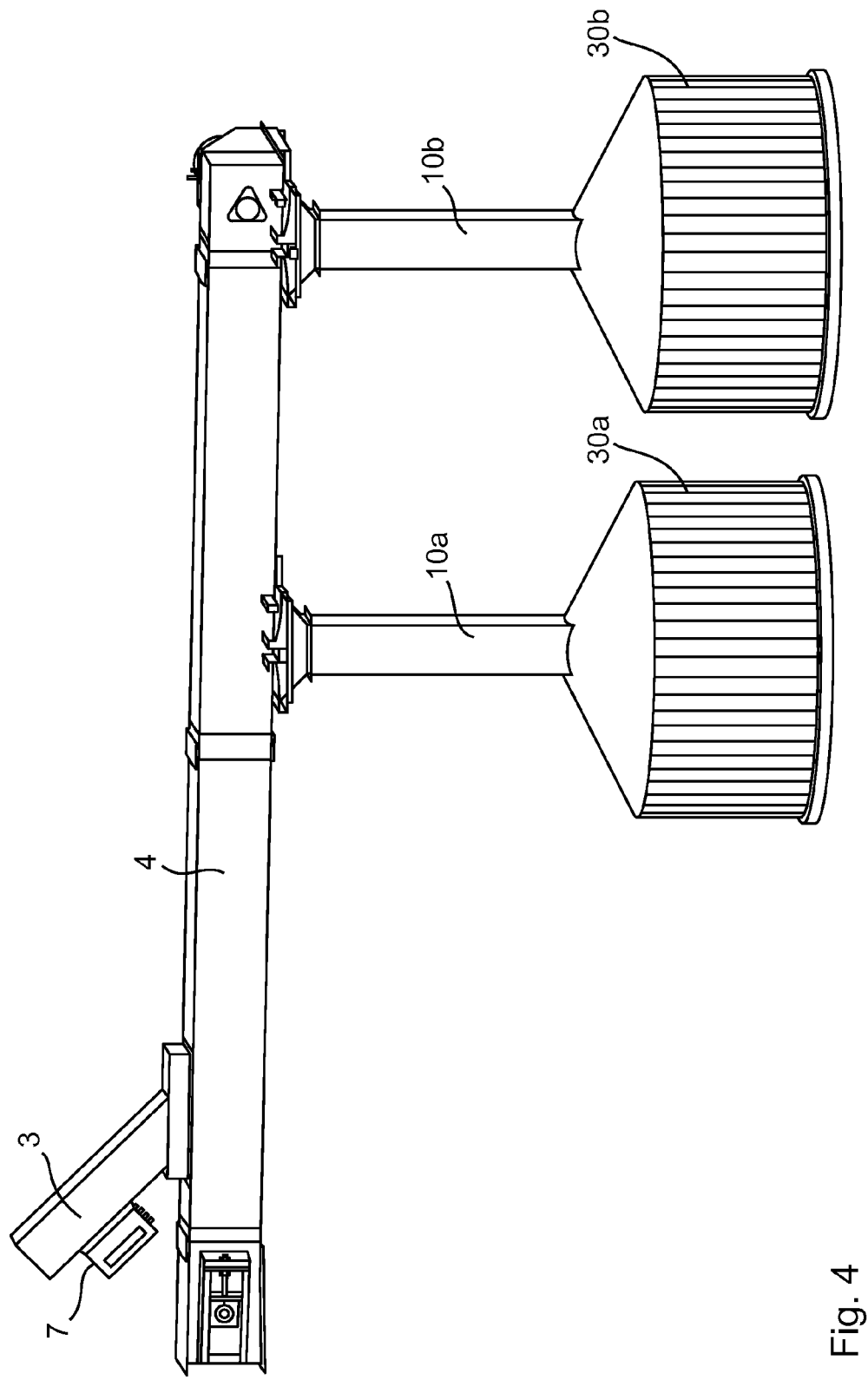
FIG. 4 is a view of one embodiment of the downstream apparatus of the invention.

Referring now to FIGS. 4 to 9 there is provided a view of different embodiments of the downstream apparatus 1. As shown in FIG. 4 the grain in-feed chute 3 is positioned at approximately a 45° angle to the conveyor 4. The sensor unit 7 is positioned exterior the grain in-feed chute 3 such that it is mounted at an angle of 90° to the grain flow. FIG. 4 also shows controlled slide 10a and end slide 10b leading to separate storage silos 30a and 30b respectively.

Figure 5:
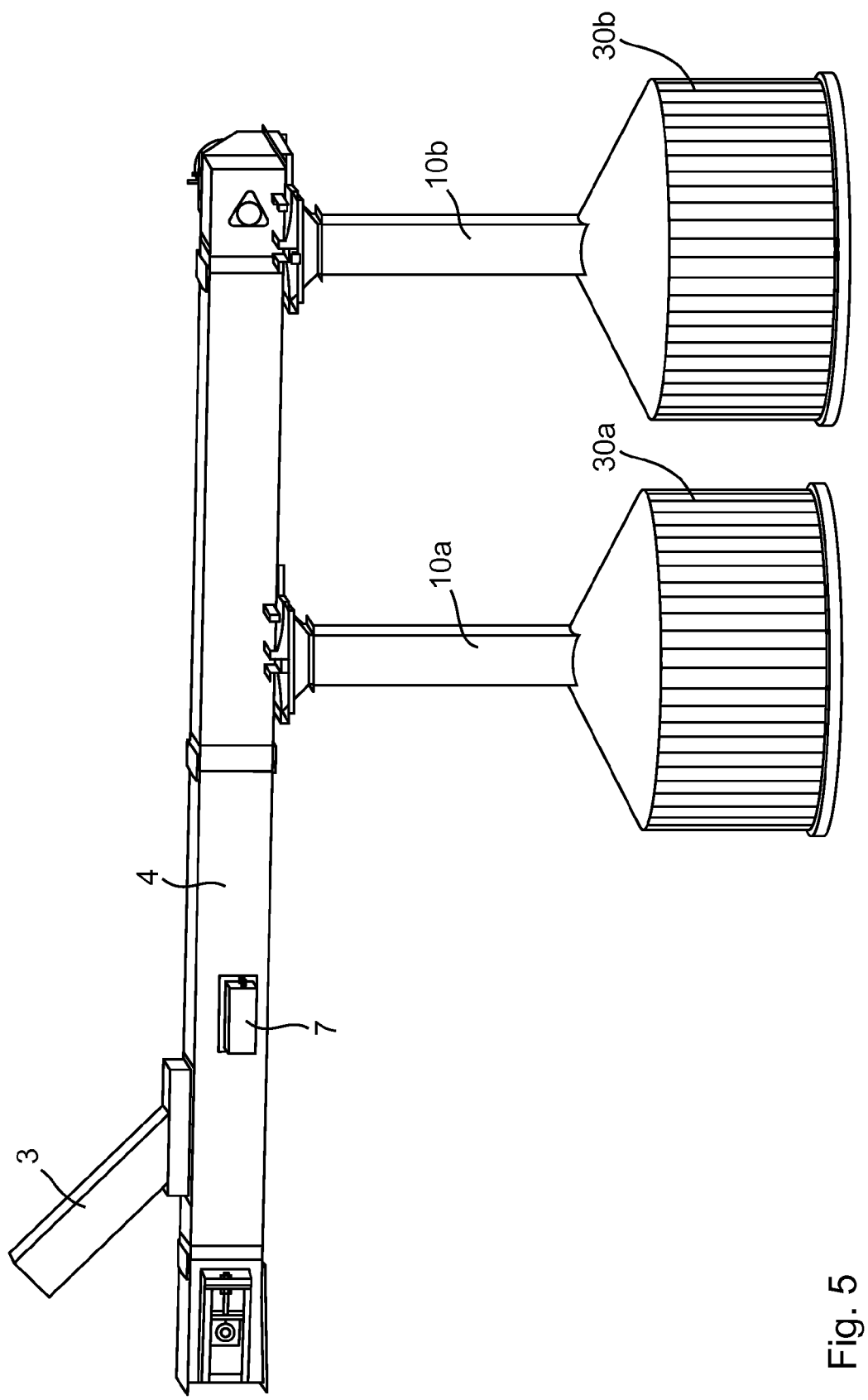
FIG. 5 is a view of another embodiment of the downstream apparatus of the invention.

FIG. 5 shows an alternative embodiment of the apparatus 1. In this embodiment the sensor unit 7 is positioned exterior of the conveyor 4 downstream of the grain in-feed chute 3. In this embodiment of the invention, the dosing slide 5 can be either positioned within the grain in-feed chute 3 upstream of the sensor unit 7 or within the conveyor 4 downstream of the sensor unit 7 so as to provide an optically dense grain layer for analysis.

Figure 6:
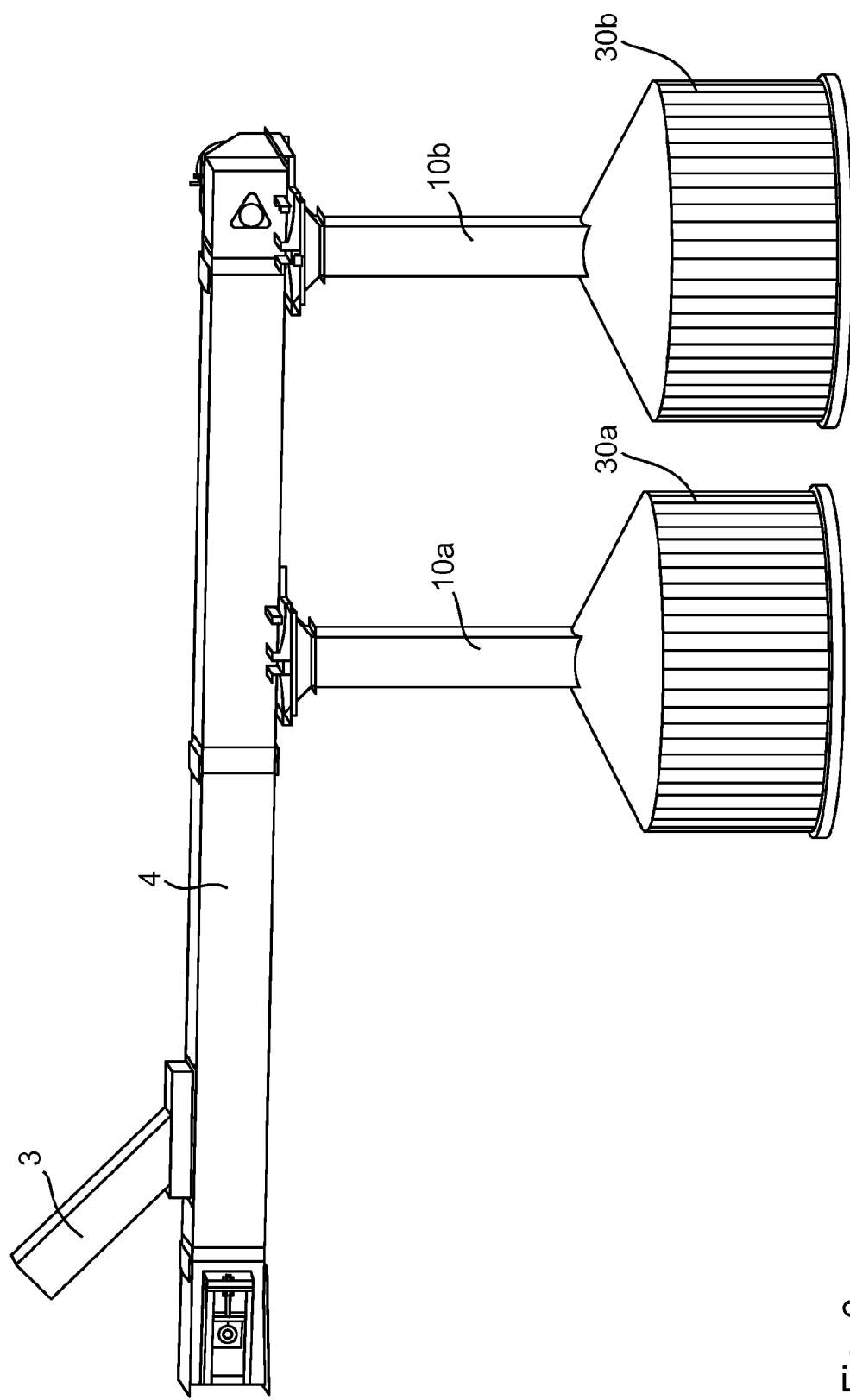
FIG. 6 is a view of a further embodiment of the downstream apparatus of the invention.

FIG. 6 shows a further alternative embodiment of the apparatus 1. In this embodiment, the sensor unit 7 is also positioned exterior of the conveyor 4 however on the opposite side of the conveyor 4 and thus not shown.

Figure 7:
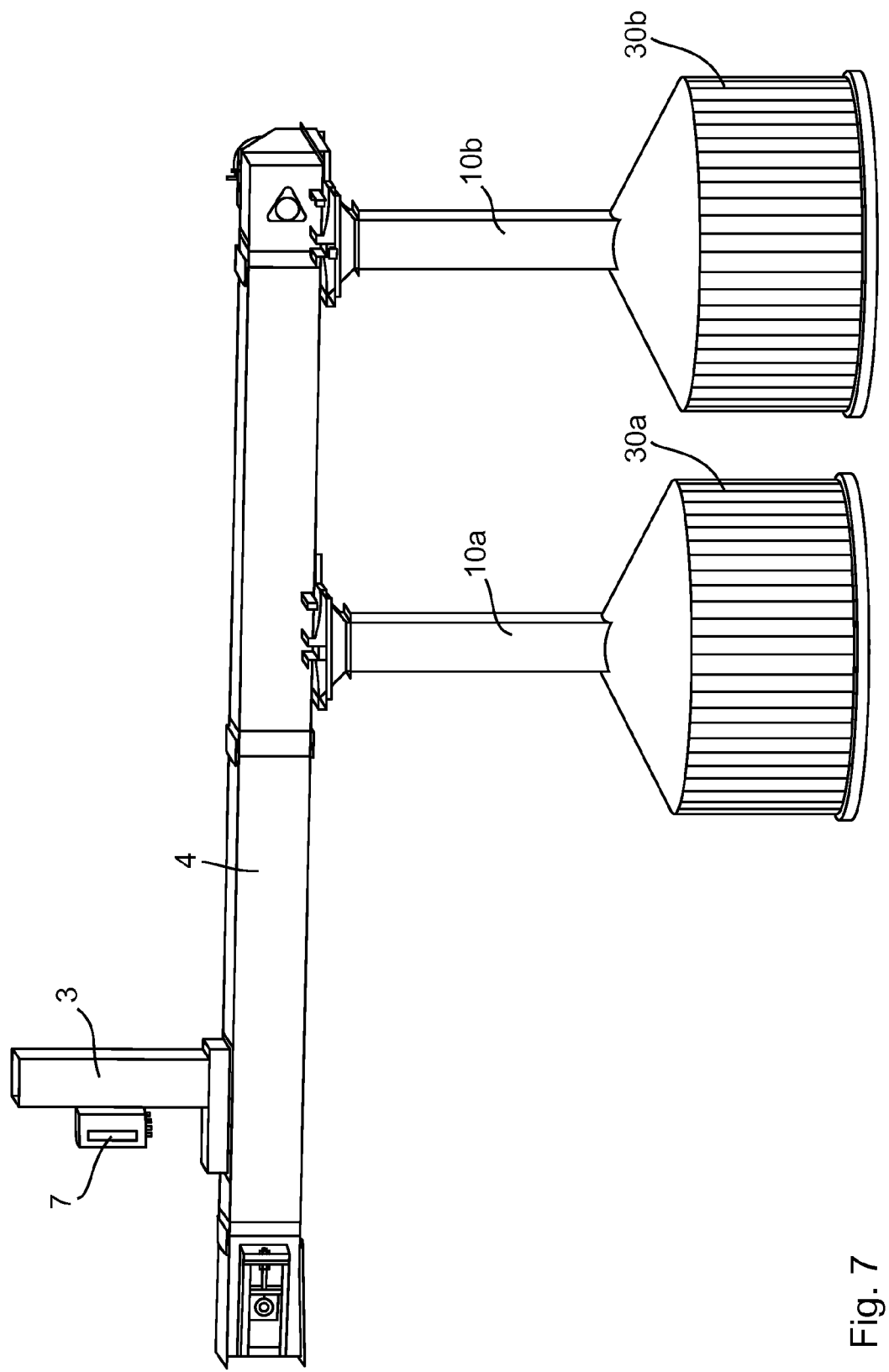
FIG. 7 is a view of another embodiment of the downstream apparatus of the invention.
Figure 8:
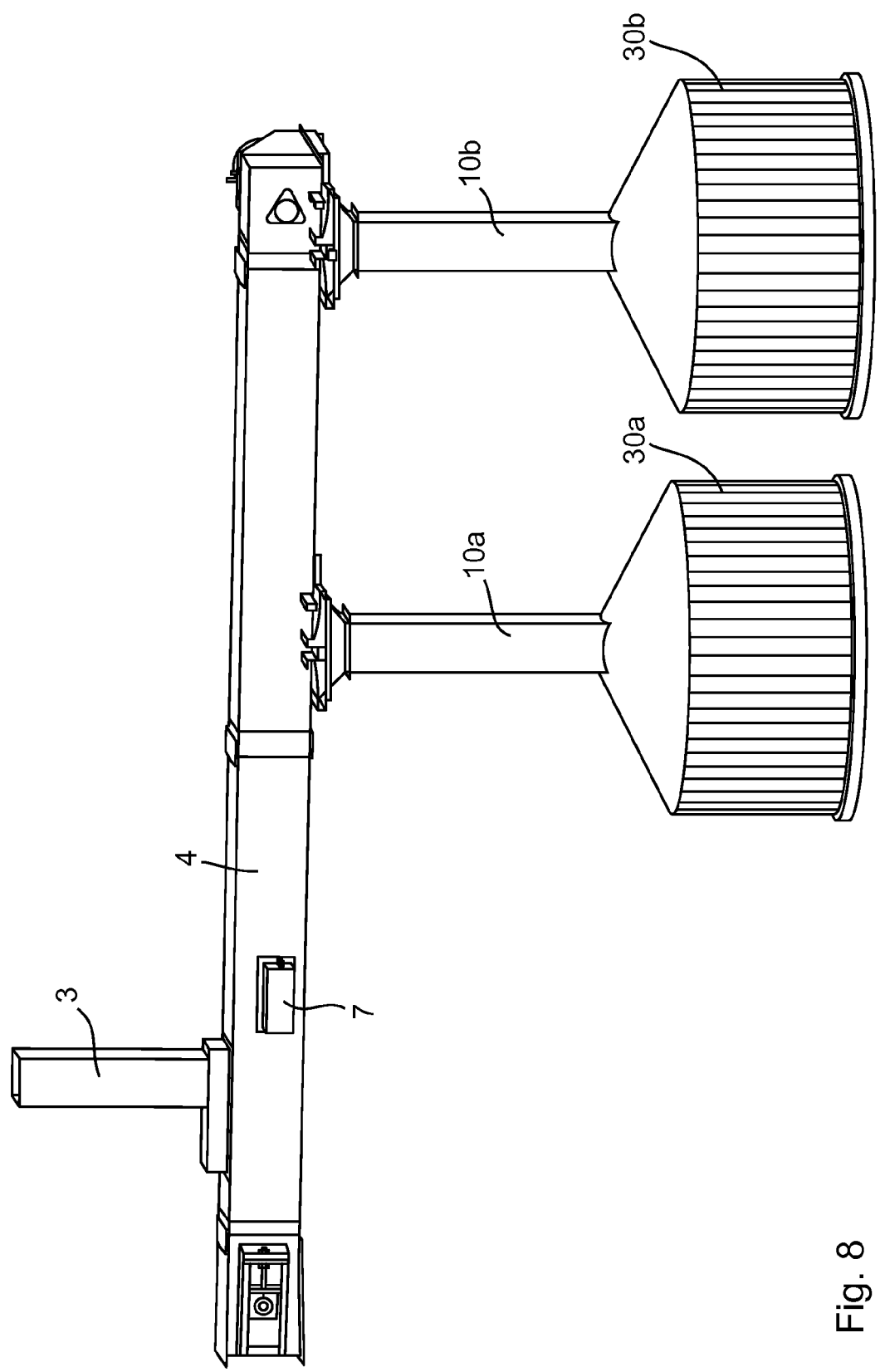
FIG. 8 is a view of a further embodiment of the downstream apparatus of the invention.
Figure 9:
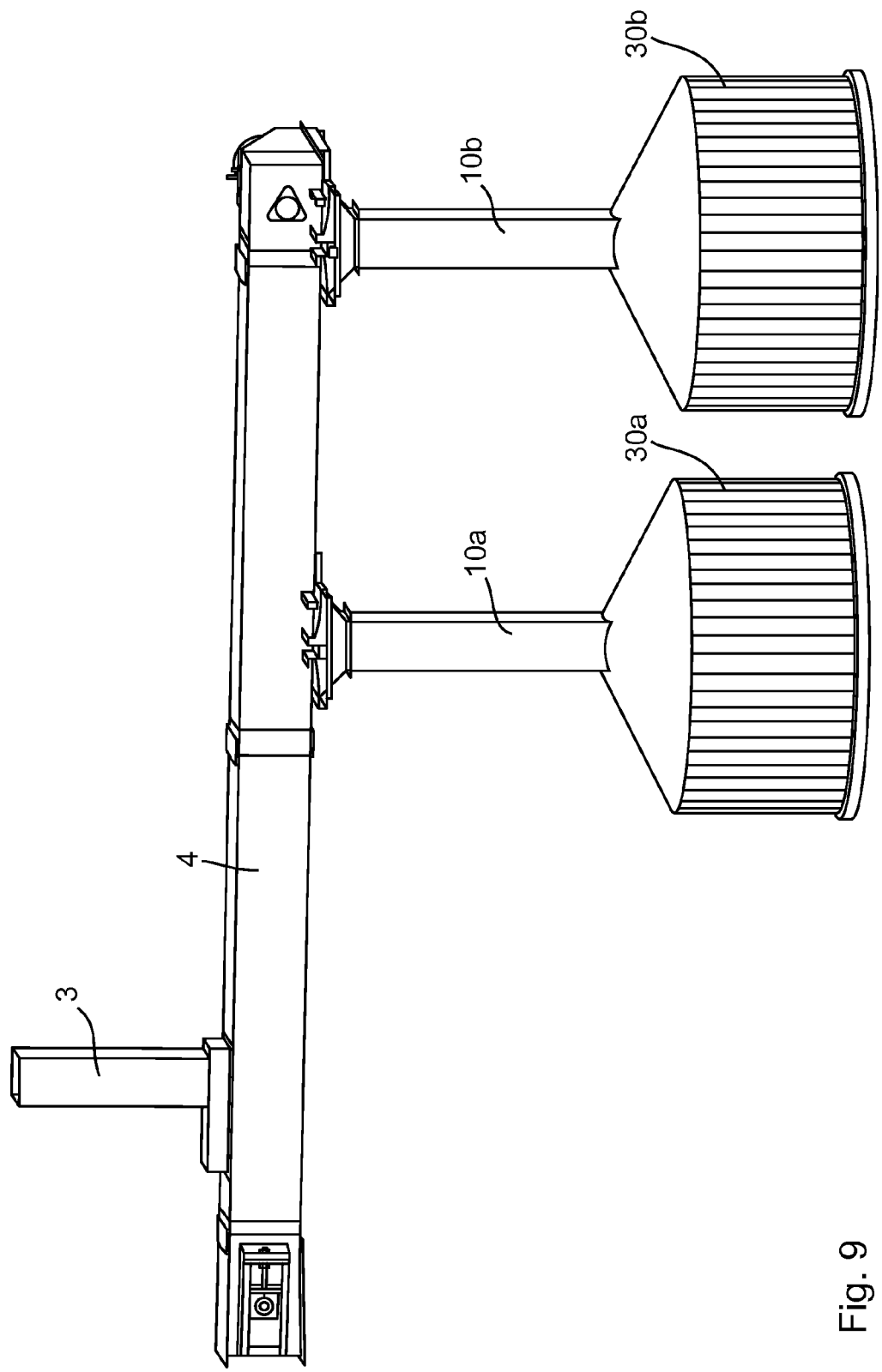
FIG. 9 is a view of a still further embodiment of the downstream apparatus of the invention.

FIGS. 7, 8 and 9 correspond to FIGS. 4, 5 and 6, with the exception that the grain in-feed chute 3 is positioned at a 90° angle to the conveyor 4. In this embodiment of the invention, the use of a grain quantity divider 20 is also preferable and a dosing slide will be provided within the grain in-feed chute 3 as above. Thus the apparatus can be applied to any industrial application where the grain in-feed chute angle may vary from between 90° (vertical) to 45°. The angle of the grain in-feed chute 3 depends on certain typical flow criteria. Such criteria include the type of grain being analysed and separated, the material of the in-feed chute, friction indices, available space for installation within silo facilities and other relevant factors.

Figure 10:
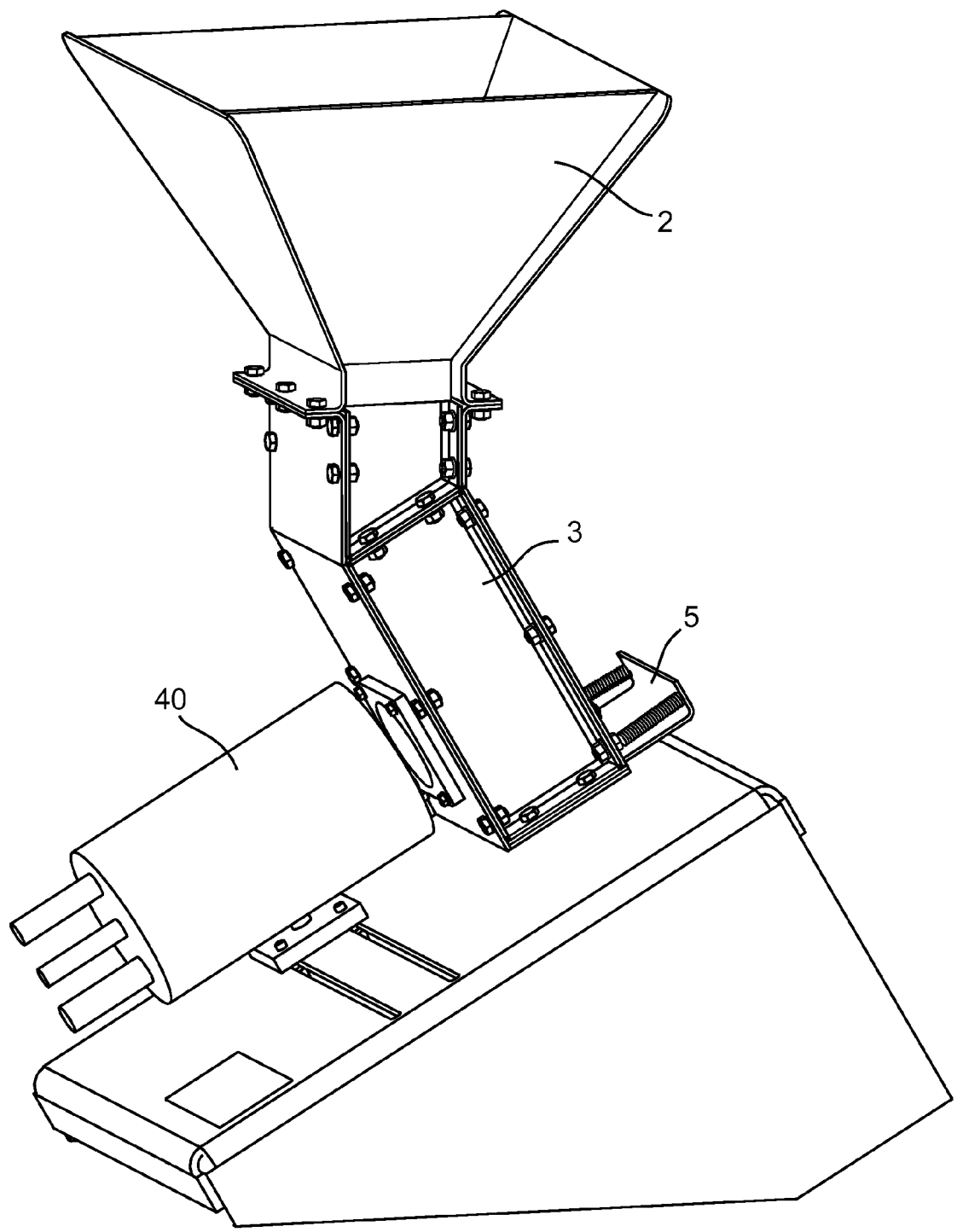
FIG. 10 is a view of a lab scale grain in-feed hopper and grain in-feed chute with a measuring head applied.

Referring to FIG. 10, there is shown a lab scale grain in-feed hopper 2 and grain in-feed chute 3 with measuring head 40 applied for calibration purposes. The measuring head 40 comprises a light source and optics and is identical to that of the measuring head housed within the sensor unit 7 of the apparatus 1. Thus identical physical optical conditions to the industrial conditions of the apparatus 1 are provided. Prior to use of the apparatus 1 validation and referencing of the apparatus 1 must be carried out for the specific type of grain and grain parameter value to be measured. A sample of the type of grain to be measured is delivered into the lab scale model and a spectrum of the grain is obtained using the measuring head 40. A spectrometer is linked to the measuring head 40 via fibre-optics (not shown) and the spectrometer is connected to a PC (not shown) with the required software to convert the received spectres into corresponding analysis values. The grain sample is then analysed using other analysis methods such as chemical analysis and a calibration curve can be derived on the basis of the analysis values for the parameter and the spectrum obtained. The calibration curve and corresponding validated calibration data will be used to convert the spectres into analysis values within the industrial scale application.

Figure 11:
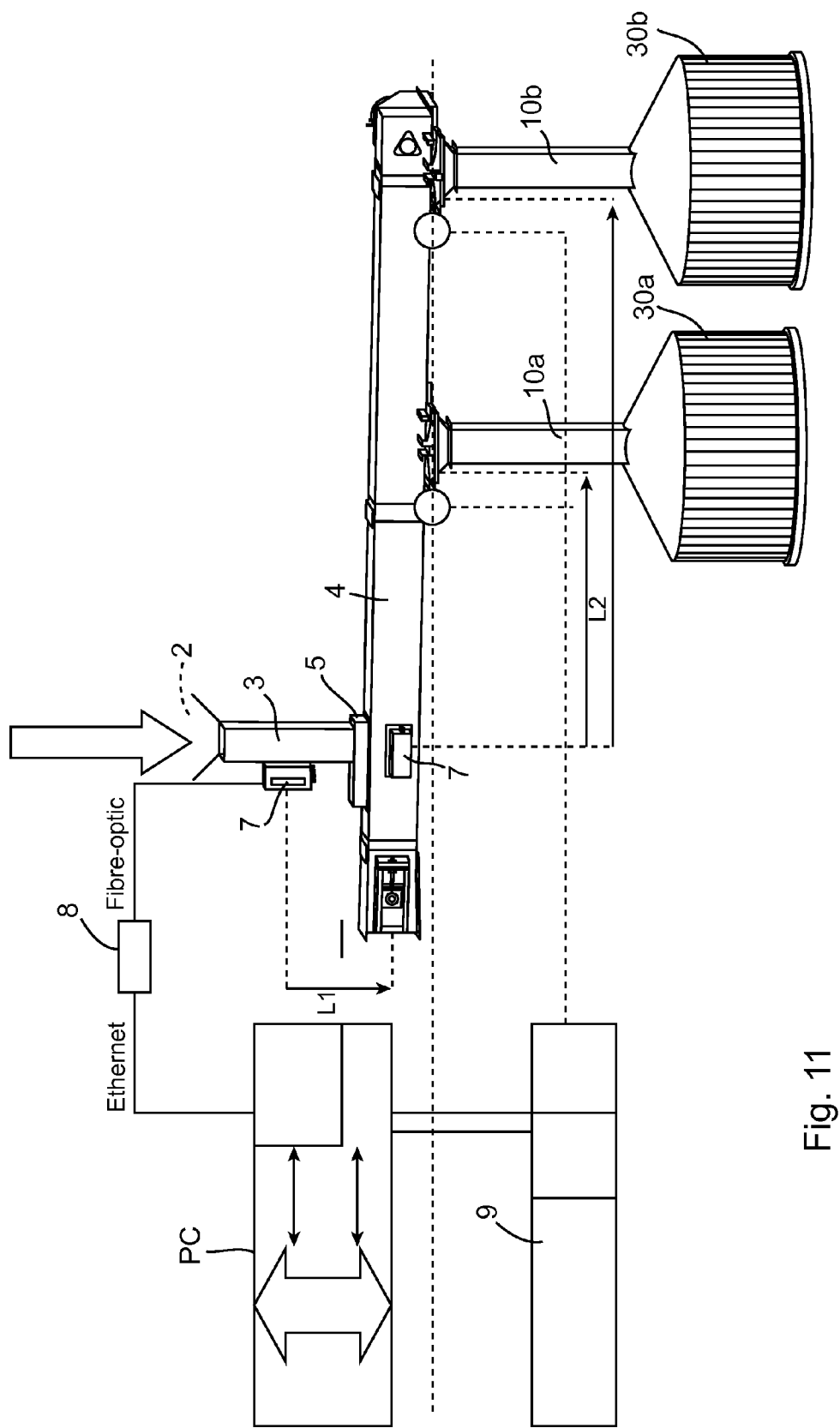
FIG. 11 is another schematic of the apparatus of the invention.

Referring to FIG. 11, in use, grain is delivered into the grain in-feed chute 3 of the apparatus 1 via the grain in-feed hopper 2. A sensor unit 7 positioned exterior to both the grain in-feed chute 3 and conveyor 4 is shown. Assuming that the sensor unit 7 positioned adjacent the grain in-feed chute 3 is active, light is continuously emitted from the light source 6 of this sensor unit 7 for a predetermined length of time onto the measurement area of the grain in-feed chute so as to emit light onto the quantity of grain passing the measurement area. An optically dense layer of grain is provided within the measurement area by the dosing slide 5 positioned down stream of the grain in-feed chute 3.

Light is reflected by the quantity of grain in the measurement area and is detected as light intensity by the sensor unit 7 to provide a spectrum of the quantity of grain. The sensor unit 7 collects the reflected light and transmits it via fibre optics to the spectrometer 8. The spectrometer 8 measures the spectre of the reflected light in the relevant wavelengths subject to grain type and analysis parameter and converts it into an electrical signal. This electrical signal will be sent via Ethernet connection and PC Interface (PCI) to a PC with specifically designed software.

The software converts this electrical signal into the respective grain parameter value by means of calibration data described above in relation to FIG. 10. The grain parameter values are recorded over time and are then converted into analog and/or digital signals. These signals are sent to the controller 9 via suitable interfaces, such as I/O cards.

The controller 9 is pre-programmed with relevant grain threshold values. Upon receipt of the grain parameter value for a particular quantity from the spectrometer 8, the controller 9 compares the grain parameter value with the grain threshold value and controls the controlled slide 10a by means of programmable pre-sets ($t_n$, $t_{lag}$) which will be discussed further in relation to FIG. 12.

Referring now to FIG. 12 there is provided a further schematic view of the apparatus 1 with each of the measurement parameters indicated. The controller 9 is pre-programmed with the relevant grain threshold values as well as other pre-sets subject to the actual design and dimensions of the apparatus 1. Thus as soon as the controller 9 receives a grain parameter value from the spectrometer 8 via the PC it will compare it to the corresponding stored grain threshold value and is programmed to send a signal to controlled slide 10a to either open or stay shut on the basis of this comparison.

As well as controlling whether the controlled slide 10a is to open or remain closed, the controller 9 can also calculate and control when the controlled slide 10a is to open and for how long the controlled slide 10a is to remain open subject to the actual series of signals received from the controller 9 on the basis of the stored values.

If there has been a sufficient change in the grain parameter value above or below the grain threshold value such that it crosses over the grain threshold value and the grain parameter value remains at that value or another sufficiently changed value for a certain length of time, the position of the controlled slide (10a) will change. If the position of the controlled slide (10a) is to change, the time ($t_n$) at which the slide [S] is to change position is calculated as a pre-set parameter programmed into the controller 9 according to the following formula:

$$t_n[S] = L_1/V_1 + L_n/V_2 + t_{lag}$$

wherein:
- $L_1$ = length from sensor unit to point y on the conveyor
- $L_n$ = length from point y on the conveyor to the controlled slide opening
- $v_1$ = speed of grain [m/s] as it passes sensor unit
- $v_2$ = speed of grain along conveyor.
- n = number of slides through which grain will pass into respective silo according to the analysis of the grain, e.g. if 2 slides, n=2.
- $t_n$ = time it takes for the specific grain quantity to get from sensor unit to that slide.
- $t_{lag}$ = "lag time" required to elapse until it will be ensured that there will be a consistent signal above/below grain threshold value in order to avoid oscillating slides or other opening means. This lag time depends also on the conveying speed, the conveyor's dimensions, the mass-flow of grain and the distance of each slide from the sensor unit. The lag times will be programmed into the controller as one or more pre-sets (e.g. for each individual slide) according to the specific dimensions and specification of the apparatus as installed.

If the sensor unit is mounted within the conveyor, then $L_1/V_1=0$ as $t_n$ will be calculated from the distance of the sensor unit to the slides/silos ($L_{1\ldots n}$) and the grain speed $V_2$ within the conveyor.

The resolution of the separation system depends on the specific conditions and the grain flow per each individual installation. The flow of grain through the apparatus is generally at a speed between 0.5 and 2.5 m/s and preferably between 1 and 2 m/s.

$t_1 = L_1/v_1$ the time that a certain mass-flow (e.g. kg/s) with a certain quality passes by the sensor unit with measuring head with one measuring operation generally taking between 15 and 70 milliseconds and preferably between 30 and 50 milliseconds.

The mass flow of grain (m) through grain in-feed chute 3 or through the conveyor 4 is adjusted with the help of the dosing slide 5. As the mass-flow through the grain in-feed chute 3 equals the mass-flow through the conveyor 4 (assuming that there must not be any leakage) the time $t_1$ can be calculated. This value is based on the speed $v_1$=speed of grain [m/s] as it passes the sensor unit 7 and $L_1$=length from sensor unit 7 to point y on the conveyor 4. The geometry of the grain layer passing by the sensor unit 7 is applied ensuring that all mass differentials passing will be fully occupied by grain in consistent flow. This is achieved by the dosing slide 5.

Using the equations specified above $t_n$ and $t_{lag}$ are calculated and input into the controller 9.

For example, assuming that moisture content is to be analysed and the grain is to be separated on the basis of its moisture content. The moisture threshold value could be set at 12%. Controlled slide 10a can be set up to deliver grain having a "low" moisture content e.g. (less than 12%) content to a silo 30a and end slide 10b will therefore deliver grain having a "high" moisture content (e.g. equal to or greater than 12%) to another silo 30b.

The apparatus 1 can be set up so that controlled slide 10a starts in an open or closed position. Assuming that controlled slide 10a starts in an open position and that the sensor unit 7 is positioned exterior the grain in-feed chute 3. Grain is continuously fed through the apparatus 1 and quantities of grain are continuously analysed as they pass the measurement area adjacent the sensor unit 7. Assuming that grain is continuously found to have a low moisture content and thus have consistent grain parameter values, controlled slide 10a is continuously kept open and this grain is delivered into silo 30a.

As soon as the controller 9 detects a quantity having a high moisture content this is detected as a sufficient change in the grain parameter value as the grain parameter value has crossed over the grain threshold value such that it is now above the grain threshold value and the controller triggers the lag time $t_{lag}$ to begin. Further quantities of grain are continuously measured until the end of $t_{lag}$. If at the end of $t_{lag}$, subsequent quantities of grain analysed have been found to have a low moisture content and thus a further sufficient change is detected such that the grain parameter value has crossed back over the grain threshold value the controlled slide 10a remains open to allow these quantities of grain with a low moisture content to exit via this controlled slide 10a to silo 30a. The lag time will not start again until a quantity with a high moisture content is detected, i.e. a further sufficient change in the grain parameter value.

If however a series of quantities of grain with a higher moisture content are measured, $t_{lag}$ will begin again and controlled slide 10a will receive a signal from the controller 9 to stay in "ready condition" to be closed and thus prepare to change position. After $t_{lag}$ has elapsed and the quantities of grain being measured have a high moisture content, the controller then sends a signal to the controlled slide 10a to close and this will ensure that the grain will exit via slide 10b to silo 30b for storage of grain with a high moisture content.

The time at which 10a is to close is $t_{lag}+t_n$ i.e. lag time plus the time it takes for that quantity to get from sensor unit 7 to controlled slide 10a. Slide 10a is continuously kept shut until the controller 9 detects a quantity having a low moisture content, i.e. a further sufficient change. At this stage $t_{lag}$ begins and slide 10a will open if at the end of $t_{lag}$ quantities with a low moisture content are still being detected.

The process continues until all of the grain has been analysed and separated.

The process and apparatus allows rapid analysis and separation of the grain in-line. Potential mechanical problems which would have been envisaged by continuous oscillation of the slide 10a are obviated by inclusion of this lag time. This allows increased flow rates of grain through the apparatus. Although it is envisaged that due to the inclusion of this lag time that small quantities of grain may be sent to the wrong silo, the overall homogeneity of the separated batches of grain will be in line with technical requirements and standards.

Delivery

A grain in-feed hopper and grain in-feed chute has been described for the continuous delivery of grain into the apparatus, it is envisaged however that other devices with the same function could also be used. The downstream delivery means has been described above as a conveyor and it is envisaged that any suitable type of grain conveyor such as for example a chain conveyor, a bucket elevator or a conveyor belt could be used.

Measurement and Analysis

The process and apparatus has been described with relation to the measurement of the protein and moisture content of grain. The protein threshold values would generally be in the range of between 10% and 12.5% by dry matter of the grain and the moisture threshold values would generally be in the range of between 12% and 18% by weight of the grain. The actual threshold value chosen will be at the discretion of the user. It is also envisaged however that other grain parameters such as for example starch extract content, β-glucan content, beta-amylase content and mycotoxine content could also be measured using this process and apparatus.

The process and apparatus is also suitable for measuring all types of grain such as for example barley, wheat, corn, rape seed, rice, malt, sorghum and pellets.

It has been found that for most accurate results that the sensor unit should be mounted at an angle in the region of 90° to the dense grain layer to be measured.

The light source, sensor unit and spectrometer can either be integrated or can be separate components located remotely from each other. Additionally the light source and light detector can be reconciled in one component (measuring head) as part of the sensor unit.

The measuring head within the sensor unit detects the light reflected by the light source. The frequency by which the electrical signal is provided by the spectrometer depends on the quality of the black and white referencing system. The PC also controls the automatic black and white referencing. This black/white referencing system must be executed once per day prior to operation of the apparatus. A step motor positions the measuring head of the sensor unit in front of a white disk and measures the total rate of photons reflected across all wavelengths ("white"=ideally 100% reflection).

In between the measuring head and the white disk a sapphire glass identical to the sapphire glass installed in between the measuring head and the grain sample passing by in the measurement area can be provided. With the white disk replacing the grain sample during white referencing all distances in between measuring head and sapphire glass, sapphire glass and white disk and/or measuring head and white disk are to be identical with those distances as installed when in the measuring position. This set-up ensures that all relevant optical factors such as e.g., focus point, friction index etc. will be factored in during the white referencing exercise.

The measuring head is then moved in front of a black tube and total absorbance of all emitted photons is measured ("black"=ideally 100% absorbance). The PC checks the correct completion of the referencing before signaling that the apparatus is ready for operation.

A suitable combined sensor unit and spectrometer for emitting light, detecting light reflected and converting a light value into a grain parameter value is the Zeiss Corona NIR™ system comprised of a measuring head OMK 500 (light emitter and detector without automatic black white referencing as part of the apparatus sensor and a spectrometer such as for example the Corona™ remote system which can perform all of these functions. Any other apparatus which also performs these functions however would also be suitable and should be calibrated prior to use.

The sensor can be mounted in either the grain in-feed chute or conveyor at any position where a dense grain layer will pass the sensor unit at a controlled, consistent grain speed. This is achieved by positioning the dosing slide downstream of the sensor unit. The spectrometer should be suitable for measuring wavelengths of between 200 and 2000 nm.

The measurement area will depend on the size of the light source and sensor unit and can be varied at the discretion of the user.

The apparatus will also comprise a central processing unit and the associated software for evaluating and converting, storing and displaying the data.

Separation

Although the apparatus is generally described above having two exits for separating grain according to whether each quantity of grain is above or below a certain threshold limit, it is envisaged that the process and apparatus of the invention would also be suitable for dividing up quantities of grain on the basis of specific ranges for a parameter and in this case the apparatus could have more than two exits. In this embodiment it is envisaged that more than one slide would be a controlled slide.

Additionally, it is further envisaged that the process and apparatus of the invention would be suitable for dividing up quantities of grain on the basis of two or more parameters. Thus for example, the grain could be divided up on the basis of protein content and moisture content at the same time. In this embodiment of the invention, the apparatus would have four exits, one for high protein, high moisture, one for high protein, low moisture, one for low protein, high moisture and one for low protein, low moisture.

In order to avoid additional lag time for opening and closing the slide, it should be mounted in a manner such that the slide opens in a flow direction counter-current to the grain flow.

It has been found that jamming of the system can be prevented by means of standard automation survey and control. One option to avoid jamming is to leave the end slide open at all times. This provides protection against grain and/or equipment damage, especially when the conveyor needs to be restarted at full load in an emergency situation. Additionally, the end slide will allow the conveyor to run 100% empty throughout its whole length at the end of the transport action.

As an alternative to rapid opening slides, any suitable opening means trap doors could also be installed between the conveyor and the slides, and these would be controlled by the controller.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiment hereinbefore described, but may be varied in both construction and detail within the scope of the claims.

The invention claimed is:

1. A process for analysing quantities of grain in-line and separating the grain into batches on the basis of one or more grain parameter values, the process comprising:
   delivering an optically dense grain layer continuously past an in-line measurement area;
   analysing a quantity of the grain by emitting light onto the grain layer, the light being reflected from the quantity of grain passing the in-line measurement area and detecting the light reflected from the quantity of grain to provide a spectrum of the quantity of grain;
   converting the spectrum into the or each grain parameter value; and
   separating the grain into batches by sorting the grain quantity on the basis of the or each grain parameter value;
   wherein the grain is separated in-line on the basis of the or each grain parameter value.

2. A process as claimed in claim 1 wherein separating the grain in-line comprises the steps of:
   storing one or more grain threshold values;
   comparing the or each grain parameter value to the corresponding stored grain threshold value;
   generating a signal based on the comparison between the or each grain parameter value and the corresponding grain threshold value;
   using the signal to effect automatic delivery of the grain quantity to a predetermined location on the basis of the grain parameter value.

3. A process as claimed in claim 1 wherein the optically dense grain layer is delivered at a speed of between 0.5 and 2.5 m/s.

4. A process as claimed in claim 1 wherein the optically dense grain layer is delivered at a speed of between 1 and 2 m/s.

5. A process as claimed in claim 1 wherein the light is emitted continuously onto the optically dense grain layer.

6. A process as claimed in claim 1 wherein the light is emitted at a wavelength of between 200 and 2000 nm.

7. A process as claimed in claim 1 wherein the light is emitted at a Near Infrared (NIR) spectral region of between 780 nm and 2000 nm and an NIR spectrum is provided.

8. A process as claimed in claim 1 wherein the light is emitted at a wavelength of between 900 and 1500 nm.

9. A process as claimed in claim 1 wherein the light is detected from the quantity of grain in a time of between 15 and 70 milliseconds.

10. A process as claimed in claim 1 wherein the light is detected from the quantity of grain in a time of between 30 and 50 milliseconds.

* * * * *

UNITED STATES PATENT AND TRADEMARK OFFICE
CERTIFICATE OF CORRECTION

PATENT NO.       : 8,569,644 B2                                                     Page 1 of 1
APPLICATION NO. : 12/513207
DATED            : October 29, 2013
INVENTOR(S)      : Nierle et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 463 days.

Signed and Sealed this
Twenty-second Day of September, 2015

Michelle K. Lee
*Director of the United States Patent and Trademark Office*